United States Patent [19]
Lai et al.

[11] Patent Number: 5,672,752
[45] Date of Patent: Sep. 30, 1997

[54] LIQUID ALKYLATED DIPHENYLAMINE ANTIOXIDANT

[75] Inventors: John T. Lai, Broadview Heights; Deborah S. Filla, Twinsburg, both of Ohio

[73] Assignee: The BFGoodrich Company, Richfield, Ohio

[21] Appl. No.: 527,475

[22] Filed: Sep. 13, 1995

[51] Int. Cl.$^6$ ............................................. C07C 209/68
[52] U.S. Cl. ............................................. 564/409
[58] Field of Search ............................................. 564/409

[56] References Cited

U.S. PATENT DOCUMENTS

| | | |
|---|---|---|
| 2,943,112 | 6/1960 | Popoff et al. |
| 3,452,056 | 6/1969 | Sundholm. |
| 3,655,559 | 4/1972 | Holt. |
| 4,824,601 | 4/1989 | Franklin. |
| 5,214,211 | 5/1993 | Kurek et al. ............................................. 564/409 |

OTHER PUBLICATIONS

Chemical Reactions on Clays by Pierre Laszlo in Science vol. 235, pp. 1473–1477, published by American Association for the Advancement of Science, Washington, D.C., Mar., 1987.

*Primary Examiner*—Brian M. Burn
*Attorney, Agent, or Firm*—Mary Ann Tucker

[57] ABSTRACT

A process for monoalkylating diphenylamine using clay catalyst is disclosed which results in a reaction product having substantial amounts of desirable monoalkylated diphenylamine and minimal amounts of less desirable disubstituted diphenylamine and unsubstituted diphenylamine. The disclosed process uses clay catalysts which favor monoalkylation over dialkylation and specific conditions such as reaction temperature and mole ratios of alkylating olefin to diphenylamine.

12 Claims, No Drawings

LIQUID ALKYLATED DIPHENYLAMINE ANTIOXIDANT

1. Field of the Invention

A process for alkylating diphenylamine which results in high amounts of desirable monosubstituted diphenylamine antioxidants is described. These monoalkylated diphenylamines have good antioxidant activity in various lubricating oils and polymeric molding compositions. These antioxidants are low in yellow color and resist further yellowing.

2. Background of the Invention

U.S. Pat. No. 2,943,112 ('112) teaches that alkylated diphenylamines are useful as antioxidants (AO). Therein it describes the alkylation of diphenylamine with relatively unreactive olefins, such as secondary alkenes (column 4, line 9–23), followed by an alkylation reaction with more reactive olefins to scavenge the unreacted diphenylamine to a concentration of less than 3%. This avoided the necessity of distilling out the undesirable unsubstituted diphenylamine. The reference mentions clay and other alkylation catalysts. Although clay offers some other processing advantages (e.g. easier separation of the catalyst from the product) the reference doesn't differentiate between the alkylation catalysts based on the proportions of mono and disubstituted diphenylamine in the reaction products.

As disclosed in U.S. Pat. No. 2,943,112 column 2, lines 26–29, monoalkylated diphenylamine is believed to be more reactive than unsubstituted diphenylamine in alkylation reactions. It was difficult to get high amounts of monoalkylated diphenylamine because as soon as the diphenylamine was monoalkyled it soon thereafter was dialkylated minimizing the amount of monoalkylated diphenylamine.

The use of clay as catalyst in the alkylation of diphenylamine is disclosed in U.S. Pat. No. 3,452,056 which describes the alkylation of diphenylamine with alpha-methyl styrene and related olefins with clay as the catalyst. In the prior art, clay was mentioned as having the advantage of giving lighter colored product and being easy to remove by filtration after the reaction. As a catalyst, clay and other Lewis Acids, such as $AlCl_3$ or $BF_3$ (column 4, line 57–69) are generally taught as being interchangeable.

U.S. Pat. No. 4,824,601 ('601) teaches liquid antioxidants are desirably (column 1, line 26–33) prepared from diphenylamine and diisobutylene at reaction temperatures above 160° C. (abstract). At the high temperatures, the octyl group was cracked to give the butyl group and perhaps the unsubstituted diphenylamine itself (column 2, line 66–68). The high temperature alkylation was continued until less than 25% dioctyldiphenylamine (DOD) was present. When diisobutylene is the alkylating olefin and the temperature is below 160° C. substantial amounts of dioctyldiphenylamine are produced. Although dioctyldiphenylamine is a liquid at the alkylation temperature, when present above 20 or 25 weight percent in the product at room temperature, it results in a solid product which is more difficult to handle or transport since it cannot be pumped from the reactor.

Unsubstituted diphenylamine is less desirable as an antioxidant because it sensitizes human skin to other irritants and tends to yellow in the composition in which they are used. High vacuum distillation can separate unsubstituted, monosubstituted, and polysubstituted diphenylamines but this is an expensive and time consuming process step.

It would be desirable to have an alkylation process for diphenylamine which would produce large amounts of monoalkylated diphenylamines and relatively small amounts of unsubstituted diphenylamine and disubstituted diphenylamine.

SUMMARY OF INVENTION

A process for alkylating unsubstituted diphenylamine is disclosed which selectively causes higher proportion of monoalkylsubstitution and produces lower amounts of less desirable unsubstituted diphenyl and/or disubstituted or polysubstituted diphenylamines than the prior art. The process uses a clay catalyst (which has greater selectivity in alkylation reactions than other alkylation catalysts) and generally uses milder conditions (e.g. lower temperatures). Disclosed olefins that result in higher proportions of monoalkylsubstitution are diisobutylene and $C_6$–$C_{18}$ linear olefins with unsaturation between the first and second carbon atom.

DETAILED DESCRIPTION

This disclosure describes the processes for making liquid and highly active antioxidants (AOs) from the alkylation of diphenylamine (DPA) with two commonly known and inexpensive olefins, namely diisobutylene (DIB) and the linear alpha-olefins.

Alkylation with diisobutylene results in a solid product when greater than 25% dioctyl DPA is formed. Special method limitations are disclosed herein to solve this problem. Unexpectedly diphenylamine can be selectively alkylated with DIB at a temperature lower than the cracking temperature of octyl groups (160°–250° C.) with a clay catalyst to give a mixture of less than 25% dioctyldiphenylamine (DOD), less than 25% DPA and greater than 50% or 55% by weight monooctyldiphenylamine (MOD) based on the total weight of the diphenylamines. The mixture can then be alkylated with isobutylene, styrene, or other reactive olefins to yield a liquid AO with less than 5% DPA, less than 20% dibutyl DPA or distyryl DPA and less than 25% preferably less than 20% DOD.

When alkylating with the relatively unreactive linear alpha-olefins (a secondary alkene with terminal unsaturation as defined in '112, column 4, line 9–13), one can either make high amounts of dialkyl DPA along with low amounts of unreacted DPA by using large excess of olefin, or one can make high amounts of monoalkyl DPA and high amounts of unreacted DPA by using deficient amount of olefin. Unexpectedly, clay is an alkylation catalyst capable of resulting in a product that has very low unreacted DPA (less than 5%) and high amounts of monoalkyl DPA, e.g., high mono:di ratio (greater than 1:1).

Monoalkylated diphenylamines are very desirable for use as antioxidants. As disclosed in U.S. Pat. No. 2,943,112 column 1, lines 28–34, if the alkyl group has six or more carbon atoms the monoalkylated diphenylamine will be low in yellow color and will resist yellowing. Di or polysubstituted diphenylamines are less effective than monosubstituted diphenylamines on a weight basis because additional alkylation significantly reduces the number of moles of diphenylamine per gram. For example diphenylamine weighs 169 g/mole, monooctyldiphenylamine weighs 281 g/mole and dioctyldiphenylamine weighs 393 g/mole.

Clay usually results in a lower degree of yellow color in the alkylated product because clay preferentially absorbs colored species. The clay is preferably an acid activated bentonite clay. $AlCl_3$ is a stronger catalyst than clay and can result in more alkylation or lower reaction temperatures than clay.

It has unexpectantly been found that clay (e.g. acid activated bentonite clay) when used as a catalyst for alkylating diphenylamine results in proportionally more monoalkylated diphenylamine than the other alkylation catalysts. When the particular olefin used and the other reaction conditions are optimized the amount of desirable monoalkylated diphenylamine can be substantial and the amounts of less desirable unsubstituted and polysubstituted diphenylamine can be kept low.

When the alkylation olefin is diisobutylene (DIB) the alkylation temperature is desirably from about 105° C. to about less than 160° C. (e.g. less than 155° C., 157° C. or 159° C.) for an hour or more, more desirably from about 110° C. to about 150° C., and preferably from about 120° C. to about 145° C. The reaction time is desirably from about 1 hour to about 5 hours, more desirably from about 2 to about 4 hours. The diphenylamine or solution of diphenylamines used as a reactant desirably has low amounts of mono, di or polysubstituted diphenylamine prior to this alkylation reaction (e.g. less than 20 or 10 weight percent based on the total of unsubstituted, mono, di and polysubstituted diphenylamines). Preferably the diphenyl amine is essentially free of (defined as less than 5 or 2 weight percent) these components (i.e. meaning the DPA has not been alkylated with another olefin). The addition of DIB to the alkylation reaction is desirably metered but may be batch, sequential or another addition method.

The disclosed process typically results in less than about 25 weight percent or less than about 20 weight percent dioctyldiphenylamine, at least 50 or 55 weight percent or at least 60 or 65 weight percent of monoalkyldiphenylamine, and less than about 25 weight percent or less than about 15 or 20 weight percent of unsubstituted diphenylamine in the reaction product. When the total monoalkylated diphenylamine is at least 55, 60 or 65 weight percent the total of the dioctyl and unsubstituted diphenylamine is less than 45, 40 or less than 35 weight percent. The monoalkylated diphenylamine is usually monooctyldiphenylamine but may include small amounts of other monoalkylated diphenylamines (e.g. less than 5 weight percent, e.g. 0.01 to about 5 weight percent) from chain scission of the diisobutylene or monooctyl group (e.g. monobutyl DPA is less than 5 weight percent and more desirably less than 3 weight percent). The amount of trisubstituted DPA is also low such as less than 5 weight percent.

These desirable percentages of products are a result of the clay catalysts preferentially catalyzing the alkylation reaction of the unsubstituted diphenylamine rather than the monoalkyldiphenylamine. The tetrahedral and octahedral layers of clay specifically and precisely repeated are believed to offer less access to the monoalkyldiphenylamine with its bulky tertiary octyl groups than the unsubstituted diphenylamine to the reactive sites in the catalysts. The monoalkylated diphenylamine is formed and converted to dialkylated or polyalkylated diphenylamine at a slower rate with clay catalyst allowing the concentration of monoalkylated diphenylamine to increase in the reaction product. Note that by specifying clay catalyst the use of amounts of AlCl$_3$, ZnCl$_3$, SnCl$_4$, H$_3$PO$_4$, BF$_3$ or other alkylation catalysts other than acidified clay is restricted to those amounts that would be ineffective to cause 10 percent or more of the total alkylation under the conditions specified.

Alternatively linear alpha olefins may also be reacted with the solution of unsubstituted diphenylamine in the presence of clay catalysts. This reaction yields increased amounts of monoalkylated diphenylamine. The linear alpha olefin can have from 6 to 18 carbon atoms and has a carbon to carbon double bond between the first and second carbon atoms of the molecule. The reaction temperature when using alpha olefins is desirable from about 130° C. to about 200° C., more desirably from about 140 to about 190° C., and preferably from about 160 to about 185° C. for at least one hour, more desirably from about 2 hours to about 10 hours, and preferably from about 4 to about 8 hours.

The reaction of linear alpha olefins with diphenylamine in the presence of clay catalyst desirably results in at least about 50 weight percent, more desirably at least about 60 weight percent and preferably at least about 65 weight percent of monoalkyldiphenylamine based on the total diphenylamines in the reaction product. Desirably it results in less than about 50 weight percent, more desirably less than about 40 weight percent, and preferably less than about 35 weight percent di or polysubstituted diphenylamines. Desirably it results in from about 0.01 to about 5 weight percent, more desirably from about 0.01 to about 2 weight percent, and preferably from about 0.01 to about 1 weight percent unsubstituted diphenylamine. Unlike dioctyldiphenylamine the disubstituted diphenylamines resulting from alkylation with linear α-olefins do not solidify the alkylation reaction product when present at concentrations above 25 weight percent.

The diphenylamine or solution of diphenylamines used as a reactant desirably has low amounts of mono, di, and polysubstituted diphenylamine prior to this alkylation (e.g. less than 20 or 10 weight percent based on the total of unsubstituted, mono, di, and polysubstituted diphenylamines). Preferably the diphenylamine or solution of diphenylamines is essentially free of (defined as less than about 5 or 2 weight percent) these components. The amount of unsubstituted diphenylamine formed during alkylation with linear α-olefins is lower than in the reaction with diisobutylene as the alkylating agent. This lower amount of unsubstituted diphenylamine is accomplished by creating more disubstituted diphenylamine which (as specified above) does not cause solidification in this alkylation reaction product. The addition of linear alpha olefins to the reaction is preferably batch but may be metered, sequential, or another addition method.

In the alkylation reaction of diphenylamine with diisobutylene in the presence of a clay catalyst the residual less than 25 weight percent or less than 20 or 15 weight percent of unsubstituted diphenylamine can be reacted with isobutylene, styrene or another reactive olefin in an alkylation reaction subsequent to the alkylation reaction with diisobutylene. This is most easily accomplished by simply adding the additional isobutylene or olefin to the reaction product from the first reaction while the clay is still present and heating the reaction mixture at temperatures from about 105° C. to less than 160° C. or the other temperatures less than 160° C. specified herein for alkylation with di-isobutylene. Note that temperatures above 160° C. are excluded to prevent cracking of the octyl groups. This reaction will result in a mixture of unsubstituted, monosubstituted (either octyl and/or the other olefin) disubstituted (either dioctyl, octyl and alkyl or styryl, dialkyl or distyryl) diphenylamine. This method for forming diisobutylene alkylated diphenylamines is preferred over the process of U.S. Pat. No. 4,824,601 because more control over the ratio and placement of octyl and butyl/non-octyl groups is possible when the cracking of octyl groups is prevented. The amount of unsubstituted diphenylamine can be reduced to less than 5 weight percent, more desirably less than 2 weight percent, and preferably less than 1 weight percent by this two step alkylation with different olefins in the first and second step. The addition of a second non-octyl olefin limits the amount of dioctyldiphenylamine formed to less than about 25 weight percent or less than about 20 weight percent so that the reaction product remains a liquid. The unreacted diisobutylene remaining from the initial alkylation can be removed from the reaction product before the other olefin (such as isobutylene) is added or may be allowed to remain and further react with the various unsubstituted and substituted diphenylamines.

The clays useful in alkylation reaction of diphenylamines are those used for bleaching oils and waxes. These are often referred to as acid activated clays. Preferred clays are sub-bentonites or bentonites which are characterized by rapid slaking when it is in the air dried state and only a slight swelling when placed in water. They consist predominantly of the clay mineral montmorillonite. The clay can be used in alkylation reactions in amounts from about 1 weight percent to about 60 percent and more desirably from about 2 to about 20 weight percent based on the amount of unsubstituted diphenylamine used as a reactant.

Commercially available clay catalysts include Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemie. These clays may include acid activated or acid leached clays. Acid activated clays are preferred. The clay catalysts may contain some water as received. Removal of the water prior to use results in a lighter colored reaction product. Therefore it is desirable to use a low water content clay or to remove the water by heating the clay with a nitrogen sweep or with vacuum stripping.

Clays are aluminosilicates. The aluminum III cations are bonded to an octahedral arrangement of oxygen anions. Repetition of these $AlO_6$ units in two dimensions formed an octahedral layer. Likewise a tetrahedral layer is formed from $SiO_4$ silicate units. Clays are classified according to the relative number of tetrahedral and octahedral layers. Montmorillonite clays, which have been used in organic chemical applications, have a octahedral layer sandwiched between two tetrahedral layers.

Although solvents have been used in alkylation reactions it is preferred in this disclosure to alkylate with minimal solvent or no solvent at all.

The unreacted olefins may be removed from the reaction product by distillation. Similarly the unreacted diphenylamine may be removed by process such as fractional distillation or vacuum distillation if necessary. The amount of diphenylamine is desirably less than about 1 or 2 weight percent in the final product. The clay can be removed by filtration or other known separation methods.

The alkylation reaction can be carried out in an autoclave if high pressures due to the vapor pressure of the olefin are anticipated. The pressure used for the reaction is primarily controlled by the olefin used and the reaction temperature. As the product is always liquid, the reactants and products may be pumped into and out of the reactor.

The commercial diisobutylene used in this disclosure can be prepared by polymerizing isobutylene. That product is predominantly a mixture of the following isomers:

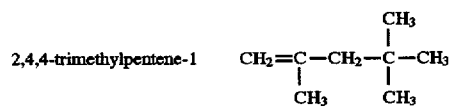

and

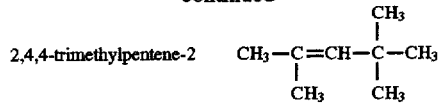

The first isomer being an alpha olefin is more reactive in alkylation reactions and is the majority of the diisobutylene and desirably is at least 60 weight percent of the diisobutylene.

In the alkylation reaction of diphenylamine with diisobutylene in the presence of clay the mole ratio of diisobutylene to diphenylamine is desirably from about 1:0.7 to about 1:1.6 and more desirably from about 1:0.8 to 1:1.3 and preferably from about 1:0.9 to 1:1.1. If the reaction product is to be reacted with a second olefin (such as isobutylene) to further reduce the residual concentration of unsubstituted diphenylamine, then the mole ratio of total diphenylamine (total of unsubstituted mono, di and polysubstituted) to that second olefin is desirably from about 1:0.2 to about 1:1.5 and more desirably from about 1:0.5 to 1:1.

In the alkylation reaction of diphenylamine with linear alpha olefins in the presence of clay the mole ratio of diphenylamine to linear alpha olefin is desirably from about 1:1 to about 1:19 and more desirably from about 1:1.1 to about 1:1.8. Most desirably it is from 1:1.2 to 1:1.5.

The alkylated diphenylamine antioxidants of this disclosure are useful to stabilize natural source and synthetic source oils and polymers from oxidative degradation during processing reactions and in their final use as lubricants or articles. They may be used in combination with other antioxidants and additives.

The following examples show the alkylation reactions of diphenylamine with diisobutylene and with linear alpha olefins.

Control

U.S. Pat. No. 4,824,601 describes an alkylation reaction where one mole of diphenylamine (169 g) was combined with 1.75 mole of diisobutylene (196 g) and 33.8 g of clay catalyst and reacted at greater than 160° C. Apparently the dioctyldiphenylamine content exceeded 25% because the reaction was continued until the reaction product had less than 25 weight percent dioctyldiphenylamine as determined by gas chromatograph (column 7, lines 27–30). The product had unsubstituted diphenylamine, monoalkylated diphenylamine and alkylated diphenylamine where the alkyl groups were independently butyl or octyl. A sample of a commercial product believed to be made by the process of U.S. Pat. No. 4,825,601 was analyzed. The commercial sample had about 16.6% t-butyl DPA, 17.3% octyl DPA, 13.3% di-t-butyl DPA, 31.7% butyloctyl DPA, 16.1% dioctyl DPA, with the remainder being unsubstituted DPA or other polysubstituted DPA. This example shows that a liquid alkylated diphenylamine can be formed by another method but the product is formed by chain scission of the diisobutylene or octyl groups into tertiary butyl substituents and results in a product having over 60% disubstituted DPA. That process only works above 160° C.

EXAMPLE 1

One mole of diphenylamine (169 g) (DPA) was reacted with one mole of diisobutylene (DIB) (112 g) in the presence of an alkylation catalyst. The reaction product included DPA, MOD (monooctyldiphenylamine), and DOD (dioctyldiphenylamine).

1 DPA + 1 DIB

+ catalyst →

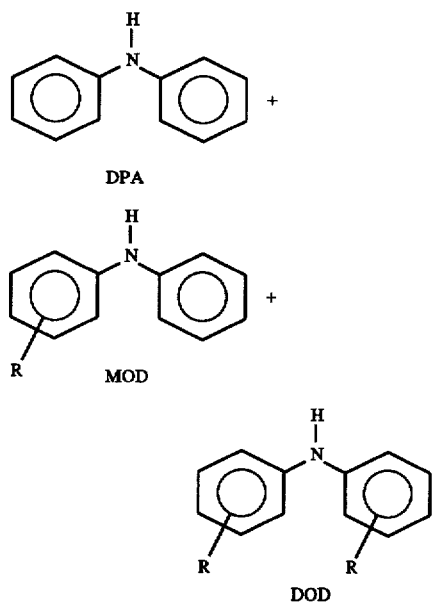

| CATALYST & CONDITIONS | PRODUCT | | |
|---|---|---|---|
| | DPA | MOD | DOD |
| 3% AlCl₃, 140° C., 1 hr | 23 WT % | 47 WT % | 30 WT % |
| 3% AlCl₃, 115° C., 2.5 hrs | 25 | 45 | 30 |
| 8% BF₃·Et₂O 115° C., 20 hrs | 24 | 50 | 26 |
| 3% SbCl₃, 140° C., 24 hrs | >95 | >5 | 0 |
| 2% Retrol™, 140° C., 2.5 hrs | 17 | 68 | 15 |

Retrol ™ is a clay catalyst.

This example shows that alkylation catalysts other than clay do not result in greater than 50 weight percent monoalkylated diphenylamine and simultaneously less than 25 weight percent dialkylated diphenylamine. As the amount of DOD is above 25 weight percent for the AlCl₃ and BF₃ catalysts further reaction or higher temperatures will only form more of the less desirable DOD. The maximum temperature with BF₃·Et₂O was 115° C. because that is the reflux temperature for BF₃·Et₂O. The SbCl₃ alkylation catalyst was not effective. The analysis of the product in this and subsequent examples was by gas chromatograph and was confirmed by mass spectrum analysis.

EXAMPLE 2

Diphenylamine (0.2 mole) and Retrol™ (1 g) were placed in a 100 ml 3-neck flask. Diisobutylene was added dropwise at 150° C. under N₂ during an one hour period. The reaction was kept at 150° C. for 1.5 more hours (a sample was taken and GC found it contained 12.7% DPA, 67.8% MOD and 17% DOD), then styrene (0.1 mole) was added over 5 minutes and the reaction was continued with heating at 150° C. for 1 hr. The reaction product was filtered with a buchner funnel and the filtrate was stripped of unreacted olefins by a simple distillation. The light-colored product was found to contain ~1% unreacted diphenylamine with the rest mixed octylated and styrylated DPA. This example shows that styrene may be used as a scavenger olefin to react with unsubstituted DPA from the disclosed process.

EXAMPLE 3

One mole of DPA (169 g) and one mole of DIB (112 g) were reacted in the presence of 3–5 weight percent Retrol™ at 145° C. for 3 hours. The product of the reaction was analyzed to be 15 weight percent DPA, 70 weight percent MOD, and 15 weight percent DOD. That mixture of DPA, MOD, and DOD was further reacted with 0.6 mole of isobutylene for 1 hour at 145° C. The product of that reaction was analyzed to be less than 1 weight percent unsubstituted diphenylamine (DPA); 12 weight percent monobutyldiphenylamine (MBD); 6 weight percent dibutyldiphenylamine (DBD); 50 weight percent monooctyldiphenylamine (MOD); 12 weight percent butyl, octyldiphenylamine (BOD); and 15 weight percent dioctyldiphenylamine (DOD). The process of this disclosure is preferred due to the 1) lighter colored product than U.S. Pat. No. 4,824,601 2) lower amounts of olefins used and 3) less expensive process because the reaction temperature is lower. The alkyl substituents may also be controlled with respect to their type and amount allowing a more uniform product to be formed than as disclosed in U.S. Pat. No. 4,824,601.

EXAMPLE 4

DPA (0.1 mole, 16.9 g) was reacted with 1-tetradecene (0.133 mole, 26.1 g) in the presence of a catalyst to form unsubstituted diphenylamine (DPA) monoalkylated diphenylamine (M14D) and dialkylated diphenylamine (D14D) where the alkyl group was tetradecane.

| CATALYST & REACTION CONDITIONS | PRODUCT | | |
|---|---|---|---|
| | DPA | M14D | D14D |
| 3.0 g Retrol ™, 175–180° C., 6 hrs | <1 WT.% | 69.9 WT % | 30.1 WT % |
| 1.3 g AlCl₃, 150° C., 8 hrs | 12.9 | 45.9 | 41.2 |
| 1.3 g AlCl₃, 175–180° C., 4.5 hrs | 8.4 | 50.7 | 40.9 |

This example shows that Retrol™, a clay, selectively forms more monoalkylated diphenylamine than other alkylation catalysts (e.g. AlCl₃). This example also shows that other alkylation catalysts form more of the less desirable disubstituted diphenylamines (having low activity on a weight basis) and leave more unsubstituted diphenylamine in the final product which is costly to remove or further react.

The above examples show that the process of this disclosure (clay catalyst, specific olefins, specific temperatures, and specified DPA:olefin ratios) forms desirable amounts of monosubstituted diphenylamines and lower amounts of less desirably di-substituted diphenylamines and unsubstituted diphenylamines.

The process minimizes or eliminates olefin cracking, minimizes the amount of olefins used, results in lightly colored products, uses mild conditions, recycles the clay catalyst, and provides more control over the final composition of the substituted DPA product. The process also provides a reaction product with higher antioxidant efficiency on a weight basis because the product has less unnecessary dialkyl substituents on the diphenylamine.

While in accordance with the patent statutes the best mode and preferred embodiment has been set forth, the scope of the invention is not limited thereto, but rather by the scope of the attached claims.

What is claimed is:

1. A process for alkylating diphenylamine, comprising:
   reacting unsubstituted diphenylamine with one or more linear olefins having from 6 to 18 carbon atoms and unsaturation between the first and second carbon atom in the presence of a clay catalyst at a temperature from about 130° to about 200° C. for at least one hour with a diphenylamine:linear olefin mole ratio of from about 1:1 to about 1:1.9, and wherein said unsubstituted diphenylamine has less than 20 weight percent of monosubstituted diphenylamine and disubstituted diphenylamine, and
   forming a mixture of diphenylamine and alkylated diphenylamines having at least 50 weight percent monoalkyl substituted diphenylamine, less than 50 weight percent of dialkyl-substituted diphenylamine, and from about 0.01 to about 5 weight percent of unsubstituted diphenylamine
   and wherein said weight percents are based on said mixture of diphenylamine and alkylated diphenylamine.

2. A process according to claim 1, wherein said temperature is from about 140° C. to about 190° C.

3. A process according to claim 2, wherein said clay is an acid activated bentonite clay.

4. A process according to claim 2, wherein said monoalkyl substituted diphenylamine is at least 60 weight percent, said mole ratio is from about 1:1.1 to about 1:1.8 and said disubstituted diphenylamine is less than 40 weight percent, said unsubstituted diphenylamine is from about 0.01 to about 2 weight percent.

5. A process according to claim 1, wherein said clay is an acid activated aluminosilicate clay.

6. A process according to claim 5, wherein said monoalkyl substituted diphenylamine is at least 60 weight percent, said disubstituted diphenylamine is less than 40 weight percent, and said unsubstituted diphenylamine is from about 0.01 to about 2 weight percent.

7. A process according to claim 6, wherein said mole ratio is from about 1:1.1 to about 1:1.8.

8. A process according to claim 7, wherein said reacting is at from about 140° C. to about 190° C. for from about 2 to about 10 hours.

9. A process according to claim 8, wherein said one or more linear olefins consist essentially of 1-tetradecene.

10. A process according to claim 6, wherein said mole ratio is from about 1:1.2 to 1:1.5.

11. A process according to claim 10, wherein said reacting is at temperatures from about 140° C. to about 190° C. for from about 2 to about 10 hours.

12. A process according to claim 11, wherein said one or more linear olefins consist essentially of 1-tetradecene.

* * * * *